United States Patent [19]

Cragoe, Jr. et al.

[11] 4,140,861

[45] Feb. 20, 1979

[54] INTERPHENYLENE 11,12-SECOPROSTAGLANDINS

[75] Inventors: Edward J. Cragoe, Jr.; John B. Bicking, both of Lansdale, Pa.

[73] Assignee: Merck & Co., Inc., Rahway, N.J.

[21] Appl. No.: 907,081

[22] Filed: May 18, 1978

Related U.S. Application Data

[62] Division of Ser. No. 751,831, Dec. 17, 1976.

[51] Int. Cl.$^2$ ............................................. C07C 69/76
[52] U.S. Cl. ...................................... 560/53; 560/55; 560/254; 562/463; 562/465
[58] Field of Search ........................... 560/53, 55, 254; 562/463, 465

[56] References Cited

U.S. PATENT DOCUMENTS

| | | | |
|---|---|---|---|
| 3,379,752 | 4/1968 | Bolhofer | 560/53 |
| 3,956,374 | 5/1976 | Shepard et al. | 560/53 |

*Primary Examiner*—Paul J. Killos
*Attorney, Agent, or Firm*—Thomas E. Arther; Harry E. Westlake, Jr.; Rudolph J. Anderson, Jr.

[57] ABSTRACT

Novel interphenylene derivatives of 11,12-secoprostaglandins are prepared by the stepwise alkylation of the ethyl ester or the t-butyl ester of acetoacetic acid. One such method involves treatment of the t-butyl ester of acetoacetic acid with a strong base to form the anion followed by treatment with ethyl p-(3-bromopropyl)-benzoate to produce ethyl 4-(4-tert-butoxycarbonyl-5-oxo-hexyl)benzoate, subsequently reacting the anion of the thus-formed benzoate with 1-chloro-4-acetoxynonane to produce ethyl 4-(4-acetyl-4-tert-butoxycarbonyl-8-acetoxytridecyl)benzoate followed by decarboxylation and alkaline hydrolysis to produce the desired product 4-(4-acetyl-8-hydroxytridecyl)benzoic acid which is useful as a pharmaceutical in the treatment of patients with renal failure and in the prevention of transplant rejection.

14 Claims, No Drawings

INTERPHENYLENE 11,12-SECOPROSTAGLANDINS

This is a division of application Ser. No. 751,831, filed Dec. 17, 1976.

SUMMARY OF THE INVENTION

This invention relates to novel interphenylene 11,12-secoprostaglandin compounds which can be represented by the following formula:

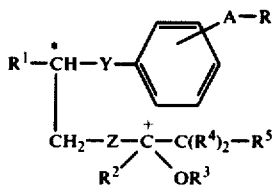

wherein R is selected from the group consisting of carboxy and a carboxy salt which incorporates a pharmaceutically acceptable cation, such as metal cations derived from alkali metals, alkaline earth metals, and amines such as ammonia, primary and secondary amines, and quaternary ammonium hydroxides. Especially preferred metal cations are those derived from alkali metals, e.g., sodium, potassium, lithium, and the like, and alkaline earth metals, e.g., calcium, magnesium, and the like and other metals, i.e., aluminum, iron, and zinc.

Pharmaceutically acceptable cations can be formed from primary, secondary, or tertiary amines, or quaternary ammonium hydroxides such as methylamine, dimethylamine, trimethylamine, ethylamine, N-methylhexylamine, benzylamine, α-phenethylamine, ethylenediamine, piperidine, morpholine, pyrrolidine, 1,4-dimethylpiperazine, ethanolamine, diethanolamine, triethanolamine, tris(hydroxymethyl)aminomethane, N-methylglucamine, N-methylglucosamine, ephedrine, procaine, tetramethylammonium hydroxide, tetraethylammonium hydroxide, benzyltrimethylammonium, and the like.

R is also selected from alkoxycarbonyl (—COOY) wherein Y is alkyl having 1-10 carbon atoms, 1-succinimidoethyl, 1-(pivaloyloxy)ethyl, 2-acetamidoethyl, or diloweralkylaminoloweralkyl; carbamoyl (—CONH$_2$); substituted carbamoyl (—CONR$^6$R$^7$) wherein R$^6$ and R$^7$ are selected from the group consisting of hydrogen, lower alkyl having 1-4 carbon atoms, and diloweralkylaminoalkyl having 4-7 carbon atoms; and carbazoyl (—CONHNH$_2$).

A is selected from a group consisting of (CH$_2$)$_n$ where n is 0, 1, or 2 and oxymethylene (—O—CH$_2$).

Y is selected from the group consisting of (CH$_2$)$_n$ where n is 1, 2, or 3 and —CH$_2$—CH=CH—.

The groups —A—R and —Y— can be located ortho, meta, or para to each other on the benzene ring.

The sum of chain-forming elements (C and O) in A and Y is limited to either 3 or 4.

R$^1$ is selected from the group consisting of acetyl, propionyl, butyryl, 1-hydroxyethyl, 1-hydroxypropyl, and 1-hydroxybutyl.

Z is selected from the group consisting of ethylene (—CH$_2$—CH$_2$—), vinylene (—CH=CH—), and ethynylene (—C≡C—).

R$^2$ is independently selected from the group consisting of hydrogen and methyl.

R$^3$ is selected from the group consisting of hydrogen and lower alkanoyl of 1-5 carbon atoms, including formyl, acetyl, propionyl, butyryl, isobutyryl, valeryl, and pivaloyl.

R$^4$ is selected independently from the group consisting of hydrogen and methyl.

R$^5$ is selected from the group consisting of lower alkyl of 3-6 carbon atoms, either straight or branched (including propyl, butyl, amyl, isoamyl, hexyl, and 3,3-dimethylbutyl), 3-butenyl, 4,4,4-trifluorobutyl, and lower alkoxy, OR$^6$, wherein R$^6$ is selected from the group consisting of lower alkyl of 2-5 carbon atoms, straight or branched (including ethyl, propyl, butyl, hexyl, isobutyl, and 3,3,3-trifluoropropyl).

In addition, when R$^5$ is lower alkyl and R$^2$ is methyl, they can be joined together (with abstraction of two hydrogen atoms) to form a carbocyclic ring with from 6 to 9 members.

Also, when R$^5$ is lower alkyl and R$^2$ is hydrogen, R$^5$ can be joined to the carbon atom bearing R$^2$ and OR$^3$ to form a carbocyclic ring with from 5 to 8 members.

It is to be recognized that the carbon atom marked by an asterisk (*) and, in some instances, the carbon atom marked by a dagger (†) are chiral. In addition, certain carbon atoms included in R$^5$ are also chiral. The compounds of this invention are understood to include the individual stereoisomers and mixtures of stereoisomers, the biological activity of which will vary but which may readily be determined in the in vitro and in vivo assays described herein.

BACKGROUND OF THE INVENTION

The compounds of formula I are described as interphenylene-11,12-secoprostaglandins. The compounds are named in this manner since they have certain structural features in common with interphenylene analogs of the natural prostaglandins. The structure of the present compounds differ from such interphenylene analogs in that they lack the cyclopentane ring characteristic of the natural prostaglandins.

The prostaglandins constitute a class of highly functionalized C$_{20}$ fatty acids. They have been shown to occur extensively in low concentrations in mammalian tissues where they are both rapidly anabolized and catabolized and to exhibit a broad spectrum of pharmacological activities including prominent roles in (a) functional hyperemia, (b) the inflammatory response, (c) the central nervous systen, (d) transport of water and electrolytes, and (e) regulation of cyclic AMP. Further details concerning the prostaglandins can be found in recent reviews of their chemistry [J. E. Pike, Fortschr. Chem. Org. Naturst., 28, 313 (1970) and G. F. Bundy A. Rep. in Med. Chem., 7, 157 (1972)]; biochemistry [J. W. Hinman, A. Rev. Biochem., 41, 161 (1972)]; pharmacology [J. R. Weeks, A. Rev. Pharm., 12, 317 (1972)]; physiological significance [E. W. Horton, Physiol. Rev., 49, 122 (1969)]; and general clinical application [J. W. Hinman, Postgrad. Med. J., 46, 562 (1970)].

The potential application of natural prostaglandins as medicinally useful therapeutic agents in various mammalian disease states is obvious but suffers from three formidable major disadvantages, namely, (a) prostaglandins are known to be rapidly metabolized in vivo in various mammalian tissues to a variety of metabolites which are devoid of the desired original biological activities, (b) the natural prostaglandins are inherently devoid of biological specificity which is requisite for a successful drug, and (c) although limited quantities of prostaglandins are presently produced by both chemical and biochemical processes, their production cost is extremely high; and consequently, their availability is quite restricted.

Our interest has, therefore, been to synthesize novel compounds structurally related to the natural prostaglandins, but with the following unique advantages: (a) simplicity of synthesis leading to low cost of production; (b) specificity of biological activity; and (c) enhanced metabolic stability so that activity can be obtained on oral as well as parenteral administration.

These advantages have been realized in the compounds of this invention. Certain of the compounds exhibit renal vasodilatory activity on oral administration and, therefore, are useful for the treatment of patients with renal impairment. Included in this group are patients with hypertension, renal failure, congestive heart failure, glomerulonephritis, uremia, and chronic renal insufficiency. The compounds of this invention by virtue of their renal vasodilatory activity improve renal function both when used alone or in conjunction with other renal agents. As example of a compound with high renal vasodilatory activity is 4-[4-acetyl-7-(1-hydroxycyclohexyl)heptyl]benzoic acid.

In addition to their activity as renal vasodilators, many compounds of this invention have useful adjunctive properties which give them added utility for the treatment of renal disease. Such properties include diuretic, saluretic, antihypertensive, and immunoregulant activities.

With regard to the indications that the compounds of this invention can be useful in therapy as regulators of the immune response, it can be stated that the basis for their activity in this area is their ability to stimulate cyclic-AMP formation in cells. Agents, including the E prostaglandins, that increase cellular cyclic-AMP concentration, interfere with the cell-mediated immune response by inhibiting lymphocyte expression in response to antigen, by inhibiting release of pathological mediators from sensitized lymphocytes, and by inhibiting the killing of target cells by such lymphocytes. Various assays which depend upon the measurement of some function of the immunologically competent lymphocyte can be used to demonostrate that the prostaglandin analogs of this invention are similarly active. For example, the release of lymphokines (proteins that are agents of inflammation and tissue destruction) from sensitized lymphocytes in culture is strongly inhibited by these analogs in low concentrations. Thus, it is apparent that the compounds of this invention are applicable to the treatment of those autoimmune diseases in whose pathogenesis a cell-mediated immune reaction is involved. Such diseases range from contact dermatitis to such chronic destructive diseases as rheumatoid arthritis and possibly multiple sclerosis and systemic lupus erythematosus. An example of a compound which is an effective regulator of the immune response is 4-(4-acetyl-8-hydroxytridecyl)benzoic acid.

Since the rejection of organ grafts is considered to be predominantly a cell-mediated immune phenomenon, a further area of usefulness of the compounds of this invention is in the prevention of transplant rejection.

The compounds of this invention can be administered intravenously, subcutaneously, intramuscularly, orally, rectally, or by aerosolization in the form of sterile implants for long action. They can be formulated in any of a number of pharmaceutical compositions and non-toxic carriers to this end.

The pharmaceutical compositions can be sterile, injectable suspensions or solutions, or solid orally-administrable, pharmaceutically acceptable tablets or capsules; the compositions can also be intended for sublingual administration, or for suppository use. It is especially advantageous to formulate compositions in dosage unit forms for ease and economy of administration and uniformity of dosage. "Dosage unit form" as a term used herein refers to physically discrete units suitable as unitary dosages for animal and human subjects, each unit containing a predetermined quantity of active material calculated to produce the desired biological effect in association with the required pharmaceutical means.

Illustratively, a sterile injectable composition can be in the form of aqueous or oleagenous suspensions or solutions.

The sterile injectable composition can be aqueous or oleagenous suspension or solution. Suspensions can be formulated according to the known art using suitable dispersing and wetting agents and suspending agents. Solutions are similarly prepared from the salt form of the compound. For the laboratory animals, we prefer to use incomplete Freund's adjuvant or sterile saline (9%) as carrier. For human parenteral use, such as intramuscularly, intravenously, or by regional perfusion, the diluent can be a sterile aqueous vehicle containing a preservative; for example, methylparaben, propylparaben, phenol, and chlorobutanol. The aqueous vehicle can also contain sodium chloride, preferably in an amount to be isotonic; as well as a suspending agent, for example, gum arabic, polyvinyl pyrrolidone, methyl cellulose, acetylated monoglyceride (available commercially as Myvacet from Distillation Products Industry, a division of Eastman Kodak Company), monomethyl glyceride, dimethyl glyceride, or a moderately high molecular weight polysorbitan (commercially available under the tradenames Tween or Span from Atlas Powder Company, Wilmington, Delaware). Other materials employed in the preparation of chemotherapeutic compositions containing the compound may include glutathione, 1,2-propanediol, glycerol, and glucose. Additionally, the pH of the composition is adjusted by use of an aqueous solution such as tris(hydroxymethyl)aminomethane (tris buffer).

Oily pharmaceutical carriers can also be used, since they dissolve the compound and permit high doses. Many oily carriers are commonly employed in pharmaceutical use, such as, for example, mineral oil, lard, cottonseed oil, peanut oil, sesame oil, or the like.

It is preferred to prepare the compositions, whether aqueous or oils, in a concentration in the range of from 2–50 mg./ml. Lower concentrations require needless quantities of liquid. Higher concentrations than 50 mg./ml. are difficult to maintain and are preferably avoided.

Oral administration forms of the drug can also be prepared for laboratory animals or human patients provided that they are encapsulated for delivery in the gut. The drug is subject to enzymatic breakdown in the acid environment of the stomach. The same dosage levels can be used as for injectable forms; however, even higher levels can be used to compensate for biodegradation in the transport. Generally, a solid unit dosage form can be prepared containing from 0.5 mg. to 25 mg. active ingredient.

Whatever the mode of administration, doses in the range of about 0.10 to 20 milligrams per kilogram of body weight administered one to four times per day are used, the exact dose depending on the age, weight, and condition of the patient, and the frequency and route of administration.

The low cost and ready accessibility of the compounds of this invention make them particularly promising for applications in veterinary medicine in which field their utilities are comparable to those in human medicine.

SYNTHESES OF PRIMARY PRODUCTS

The novel compounds which are obtained by the primary synthetic procedures with which this invention is concerned are those of formula I in which R is carboxy, $R^1$ is lower acyl (acetyl, propionyl, butyryl), and $R^3$ is hydrogen, all other groups being as defind for formula I. These primary products may thus be represented by the following formula:

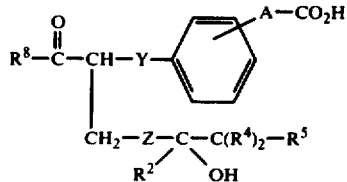
II wherein $R^8$ is methyl, ethyl, or propyl, and other groups are as defined previously.

The method of synthesis of compounds of formula II depends on the nature of groups Z and $R^2$.

1. If Z is ethylene and $R^2$ is hydrogen, the preferred process begins with a tert-butyl ester of a β-keto ester represented by formula III:

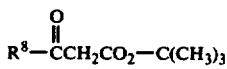
III

This keto ester is converted to its anion with a strong base, preferably sodium hydride, in a solvent or solvent mixture such as benzene-dimethylformamide. The anion in solution is treated with an alkylating agent of formula IV:

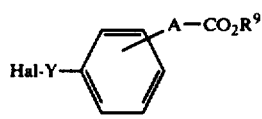
IV wherein $R^9$ is lower straight chain alkyl, preferably ethyl or methyl; Hal is chlorine, bromine, or iodine; and A and Y are as defined previously. The product obtained from this alkylation is represented by formula V:

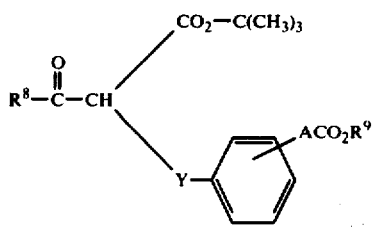
V

Keto ester V is then converted to its anion with strong base as described above and the anion in solution treated with an alkylating agent of formula VI:

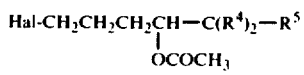
VI wherein Hal is chlorine, bromine, or iodine; and $R^4$ and $R^5$ are as defined previously. The product of this alkylation is represented by formula VII:

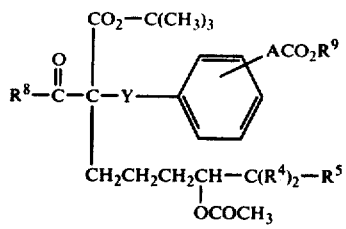
VII

It should be noted that the order of alkylation is immaterial. Thus, VII may be obtained by alkylating III first with VI and then with IV.

The compounds of formula VII are then subjected to conditions to effect elimination and decarboxylation and yield compounds of formula VIII:

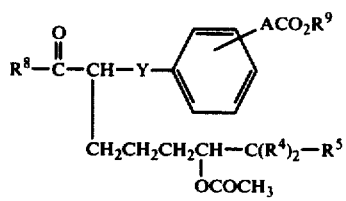
VIII

The reactions conditions used to obtain VIII are preferably either heating VII in an inert solvent at temperatures of 120°–160° C. with a trace of strong acid or treating VII at 30°–60° C. with trifluoroacetic acid.

Finally, compounds VIII are subjected to hydrolysis, preferably with strong base (KOH, NaOH) in mixtures of water and lower alcohols at 25°–80° C., to yield primary products of this invention represented by formula IIA:

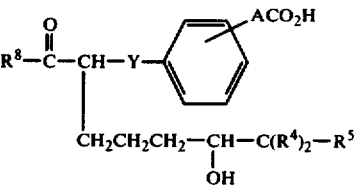
IIA

2. If Z is vinylene or ethynylene ($Z^1$) and/or $R^2$ is methyl or $R^5$ is joined to $R^2$ or to the carbon atom bearing $R^2$ and $OR^3$ to form a carbocyclic ring, the process begins with a lower straight chain alkyl ester (preferably ethyl or methyl) of a β-keto ester represented by formula IX:

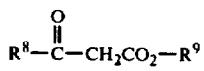
IX wherein $R^8$ and $R^9$ are as defined previously.

This keto ester is converted to its anion with a strong base, preferably sodium hydride in a solvent or solvent mixture such as diglyme or benzene-dimethylformamide. The anion in solution is then treated as in the first process with an alkylating agent of formula IV to give an intermediate of formula X:

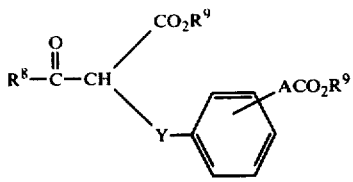

Keto ester X is then converted to its anion with strong base as described above and the anion treated with an alkylating agent of formula XI:

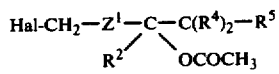

wherein Hal, $R^4$ and $R^5$ are as defined as previously, $Z^1$ is vinylene or ethynylene, and $R^2$ is methyl or part of a carbocyclic ring in connection with $R^5$.

The product of this second alkylation is represented by formula XII:

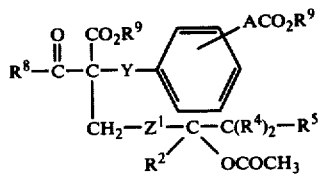

Compounds XII are subjected to basic hydrolytic conditions, preferably boiling solutions of sodium or potassium hydroxide in mixtures of water and lower alcohols. Cleavage of the three ester functions occurs. Acidification of the reaction solutions effects decarboxylation of the tertiary carboxy group. There are obtained a group of the primary products of this invention represented by formula IIB:

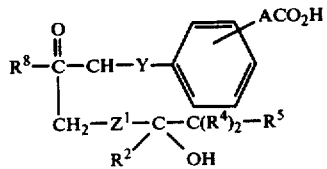

DERIVATIZATION OF PRIMARY PRODUCTS

1. When the groups Y and $Z^1$ in alkylating agents IV and XI ae unsaturated (i.e., contain double or triple bonds), the primary products derived from them will be unsaturated; i.e., they will have one or more double or triple bonds in groups Y and Z. Such primary products can be hydrogenated over platinum or palladium catalysts to yield further saturated products of this invention of formula I wherein A is a saturated chain $((CH_2)_n,$ n = 1, 2, or 3) and Z is ethylene.

2. The primary products are carboxylic acids. To obtain carboxy salts, the acid products are dissolved in a solvent such as ethanol, methanol, glyme, and the like, and the solution treated with an appropriate alkali or alkaline earth hydroxide or alkoxide to yield the metal salt, or with an equivalent quantity of ammonia, amine, or quaternary ammonium hydroxide to yield the amine salt. In each instance, the salt either separates from the solution and may be separated by filtration; or, when the salt is soluble, it may be recovered by evaporation of the solvent. Aqueous solutions of the carboxylic acid salts can be prepared by treating an aqueous suspension of the carboxylic acid with an equivalent amount of an alkaline earth hydroxide or oxide, alkali metal hydroxide, carbonate or bicarbonate, ammonia, an amine, or a quaternary ammonium hydroxide.

To obtain carboxy esters (i.e., compounds where R is alkoxycarbonyl), the acid products are treated in ether with an ethereal solution of the appropriate diazoalkane. For example, methyl esters are produced by reaction of the acid products with diazamethane. To obtain products where R is carbamoyl, substituted carbamoyl, or carbazoyl, the acid product is first converted to an active Woodward ester. For example, the acid product can be made to react with N-tert-butyl-5-methylisoxazolium perchlorate in acetonitrile in the presence of a base such as triethylamine to yield an active ester in which R is

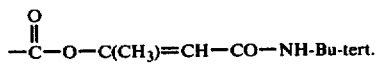

Active esters of this type can be reacted with ammonia to yield products of formula I where R is carbamoyl, with primary or secondary amines or di-lower-alkylaminoalkylamines to yield products where R is substituted carbamoyl, i.e., $-CONR^6R^7$, and with hydrazine to yield products where R is carbazoyl.

3. The primary products contain a hydroxy group; i.e., $R^3$ in formula I is hydrogen. In compounds containing no additional hydroxy group and in which $R^2$ is hydrogen, reaction with formic acid, acetic anhydride, propionic anhydride, butyric anhydride, isobutyric anhydride, valeric anhydride, pivalic anhydride, and the like, without solvent and at temperatures from 25° to 60° C., gives compounds wherein $R^3$ is formyl, acetyl, propionyl, butyryl, isobutyryl, valeryl, and pivaloyl, respectively.

4. The primary products contain an acyl group,

The carbonyl function in this acyl group can be reduced to an alcoholic functional group by the action of sodium or potassium borohydride. The following transformations are hereby effected in

acetyl becomes 1-hydroxyethyl, propionyl becomes 1-hydroxypropyl, and butyryl becomes 1-hydroxybutyl. This reduction can be advantageously carried out by dissolving the acyl-containing compound in an aqueous or alcoholic solution of a base such as sodium hydroxide, sodium bicarbonate, and the like and adding a 20 to 100% excess of sodium or potassium borohydride.

The reaction is allowed to proceed at a temperature of from 20° to 60° C. for a period of 2 to 24 hours.

PREPARATION OF THE REAGENTS

I. The reagents IV which have the following general formula:

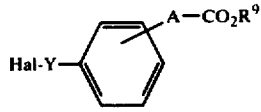

wherein Hal, $R^9$, A, and Y are as described previously are a broad group of compounds, some of which have been described in the chemical literature. No single, general method of synthesis can be prescribed for the remainder of these compounds; a variety of known organic reactions can be selected for their preparation depending on the length and nature of the chains A and Y and the orientation of these chains on the benzene ring (ortho, meta, or para). The following examples are chosen to illustrate the procedures that are most useful in the preparation of the reagents IV.

(a) Reagents IV with Para Orientation

1. When Hal is Br, $R^9$ is ethyl, A is $(CH_2)_o$ (a single bond), Y is —$(CH_2)_3$—, and A and Y are in the para orientation, reagent IV become ethyl 4-(3-bromopropyl)benzoate (XIII):

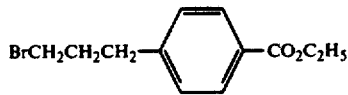

In the preparation of XIII, 3-bromopropylbenzene is acylated with aluminum chloride and acetyl chloride; the resulting acetophenone is oxidized with sodium hypobromite to 4-(3-bromopropyl)benzoic acid and the acid is esterified with ethanol and mineral acid to afford XIII.

2. When Hal is Cl, $R^9$ is ethyl, A is —O—$CH_2$—, Y is $CH_2$, and A and Y are para, the reagent IV becomes ethyl 4-chloromethylphenoxyacetate (IX):

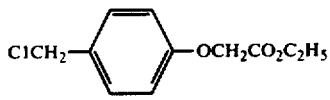

Reagent IX is prepared by the chloromethylation of ethyl phenoxyacetate, which procedure consists of heating ethyl phenoxyacetate with formaldehyde and concentrated hydrochloric acid.

3. When Hal is Br, $R^9$ is ethyl, A is $CH_2$, Y is $(CH_2)_2$, and A and Y are para, the reagent IV becomes ethyl [4-(2-bromoethyl)phenyl]acetate (X):

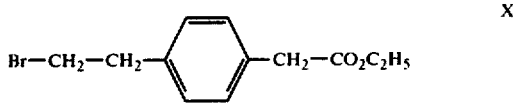

Reagent is X prepared from the known p-cyanomethylhydrocinnamic acid. This acid is first subjected to the Hunsdiecker reaction (treatment with red mercuric oxide and bromine in carbon tetrachloride solution) to obtain [4-(2-bromoethyl)phenyl]acetonitrile. The nitrile is hydrolyzed by being heated in a solution of 48% hydrobromic acid and acetic acid, and the resulting acid is esterified with ethanol and mineral acid catalyst to yield the reagent X.

(b) Reagents IV with Meta Orientation

1. When Hal is Br, A is $(CH_2)_o$ (a single bond), Y is —$CH_2$—$CH$=$CH$—, $R^9$ is methyl, and A and Y are meta, the reagent IV becomes methyl 3-(3-bromo-1-propenyl)benzoate (XI):

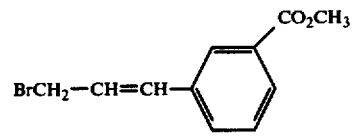

Reagent XI is prepared from the known methyl 3-bromomethylbenzoate. This halide is heated in xylene solution with triphenylphosphine to yield (3-methoxycarbonylbenzyl)triphenylphosphonium bromide. The phosphonium salt is converted to the ylide with sodium methoxide in methanol and the ylide caused to react with acetaldehyde to afford methyl 3-(1-propenyl)benzoate. This ester is heated with N-bromosuccinimide in carbon tetrachloride for an extended period to yield the reagent XI.

It should be noted that reagent XI is the functional equivalent of a reagent XII:

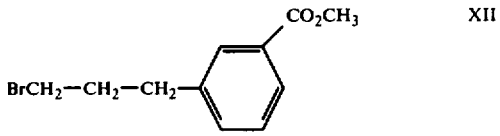

wherein Y is $(CH_2)_3$ for the following reason. When t-butyl acetoacetate is alkylated with reagent XI, the product in the Scheme below can be hydrogenated to product 2, which is the same compound as obtained by alkylation of t-butyl acetoacetate with reagent XII:

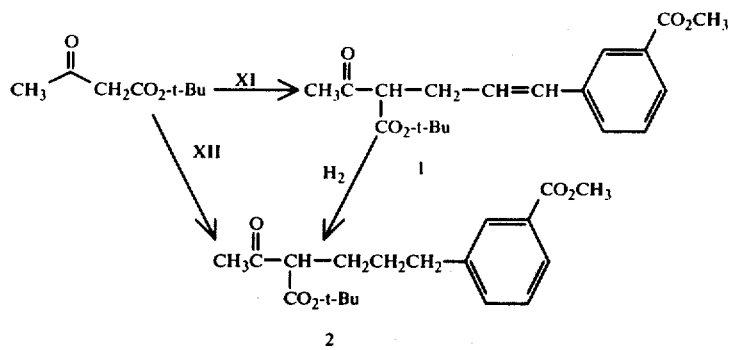

2. When Hal is Br, $R^9$ is ethyl, A is $(CH_2)_2$, Y is $CH_2$, and A and Y are meta, reagent IV becomes ethyl m-bromomethylhydrocinnamate (XIII):

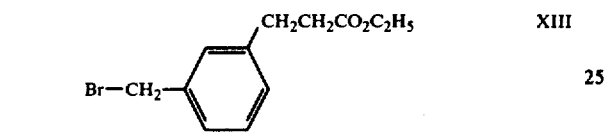

Since reagent XIII is difficult to prepare, it is advantageous to use its functional equivalent, the reagent XIV shown below. Alkylation of t-butyl acetoacetate with XIV gives a product (3) which can be hydrogenated to give the same intermediate (4) which would be obtained on alkylation of t-butyl acetoacetate with XIII:

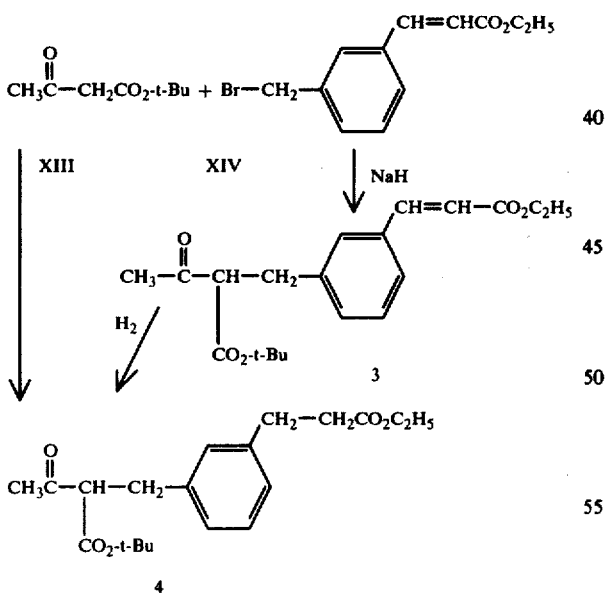

Reagent XIV (ethyl m-bromomethylcinnamate) is prepared by the reaction of N-bromosuccinimide with ethyl m-methylcinnamate in carbon tetrachloride solution.

(c) Reagents IV with Ortho Orientation

1. When Hal is Br, $R^9$ is ethyl, A is $CH_2$, Y is $(CH_2)_3$, and A and Y are ortho, reagent IV becomes ethyl [2-(3-bromopropyl)phenyl]acetate (XV):

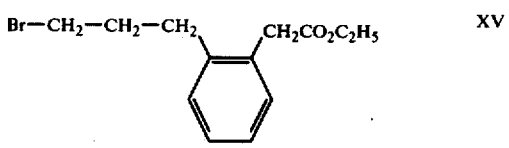

Reagent XV is prepared from ethyl o-bromomethylcinnamate by the following series of reactions. (1) The starting ester is heated with a solution of sodium cyanide in ethanol to yield ethyl o-cyanomethylcinnamate. (2) This ester is hydrogenated over a Pt or Pd catalyst to afford ethyl o-cyanomethylhydrocinnamate. (3) This ester is reduced with sodium bis(2-methoxyethoxy)aluminum hydride in benzene to yield [2-(3-hydroxypropyl)phenyl]acetonitrile. (4) The nitrile is hydrolyzed by being heated with aqueous-ethanolic sodium hydroxide solution, and the acid is esterified (ethanol and mineral acid catalyst) to give ethyl [2-(3-hydroxypropyl)-phenyl]acetate. (5) This hydroxyester is treated with phosphorous tribromide in ether to afford reagent XV.

2. The reagents VI which have the following general formula:

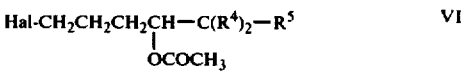

wherein Hal, $R^4$, and $R^5$ are as described previously are prepared by three related processes:

a. In the most general process, a Grignard reagent $R^5$—$C(R^4)_2$—MgBr(or MgI) is allowed to react in ether or tetrahydrofuran with a 4-halobutyronitrile, Hal—$CH_2CH_2CH_2CN$. The immediately resulting imine is hydrolyzed in aqueous acidic solution to give ketones of the formula Hal—$CH_2CH_2CH_2$—C(=O)—$C(R^4)_2$—$R^5$. The ketones are reduced to the alcohols Hal—$CH_2CH_2CH_2CH(OH)$—$C(R^4)_2$—$R^5$ with sodium or potassium borohydride in a suitable solvent such as methanol, ethanol, or diglyme. Acetylation of these alcohols preferably with acetic anhydride gives the reagents VI.

b. A variant of this process that is particularly useful when both $R^4$ groups are methyl consists in reacting Grignard reagents $R^5$—$C(CH_3)_2$—MgCl with 4-halobutyryl chlorides, Hal—$CH_2CH_2CH_2COCl$. The resulting ketones, Hal—$CH_2CH_2CH_2C(=O)$—$C(R^4)_2$—$R^5$, are reduced to the alcohols and acetylated as above in a. to give the reagents VI wherein $R^4$ is methyl.

c. A third process is particularly useful when $R^5$ is lower alkoxy, $OR^6$, where $R^6$ is as defined previously. Here, the Grignard reagent prepared from ethylmagnesium bromide and the known tetrahydro-2-(2-propynyloxy)-2H-pyran is caused to react with alkoxyacetaldehydes $R^6$—O—$C(R^4)_2$CHO. Treatment of the reaction mixture with acetic anhydride and the usual workup affords the intermediates THP—O—$CH_2$C≡C—$CH(OCOCH_3)$—$C(R^4)_2$—O—$R^6$ (THP=tetrahydropyranyl). Hydrogenation of this intermediate over a palladium catalyst and hydrolysis of the tetrahydropyranyl group in aqueous-alcoholic hydrochloric acid solution affords the alcohol, HO—$CH_2CH_2CH_2$C$H(OCOCH_3)$—$C(R^4)_2$—$OR^6$. The alcohol is converted to its tosylate ester with p-toluenesulfonyl chloride in pyridine. The tosylate ester is treated with a solution of sodium iodide in acetone to effect displacement of the tosylate group and yield reagents of formula VI where Hal is iodo and $R^5$ is lower alkoxy, $OR^6$.

3. The methods that are selected for the preparation of reagents XI:

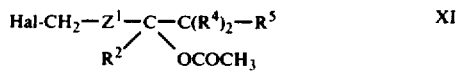
XI (wherein $Z^1$ is vinylene or ethynylene) depend on the nature of $Z^1$.

a. When $Z^1$ is vinylene, a particularly useful method consists in treating an α,β-unsaturated carbonyl compound $CH_3CH$=CH—C(=O)—$R^2$ with Grignard reagents $R^5$—$C(R^4)_2$—MgBr(or MgBI). The products of this reaction obtained after the usual workup are

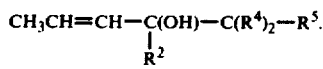

These alcohols are acetylated, preferably with acetic anhydride, to give the acetoxy intermediates

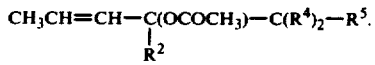

These intermediates are allowed to react with N-bromosuccinimide in carbon tetrachloride at 50°-70° C. for 2.5 to 5 hours to effect allylic bromination and give the reagents XI where Hal is bromo and $Z^1$ is vinylene.

b. When $Z^1$ is ethynylene, a process is selected that is of further advantage in that it can be used for the preparation of those compounds where $R^5$ and $R^2$ (methyl) are joined together to form carbocyclic rings. The starting materials for the process are aldehydes or ketones with the structure $R^2$—C(=O)—$C(R^4)_2$—$R^5$. Examples of such aldehydes and ketones are hexanal, 2-methylhexanal, 2-heptanone and (when $R^5$ is joined either with $R^2$ when $R^2$ is methyl or with the carbon bearing $R^2$ when $R^2$ is hydrogen as earlier specified) cyclohexanone or cyclooctanone. Such aldehydes or ketones are caused to react with lithium acetylide or ethynylmagnesium bromide to give alcohols of the structure

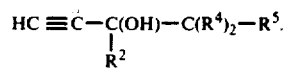

These alcohols are acetylated preferably with acetic anhydride in pyridine solution. The resulting acetates are heated with formaldehyde (preferably introduced in the form of paraformaldehyde) and dimethylamine or diethylamine to give amines $Me_2N$— or

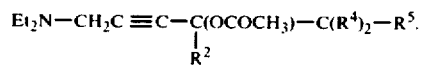

The amines are caused to react with cyanogen bromide preferably in ether solution at 25°-35° C. and from 8 to 24 hours to give the reagents XI where Hal is bromo and $Z^1$ is ethynylene.

This process is also of particular advantage in preparing alkylating intermediates XI used for the synthesis of the compounds of formula I wherein the chiral carbon atom bearing $R^2$ and $OR^3$ is exclusively in either the R or the S configuration. Such alkylating agents can be represented by the formula XI-A:

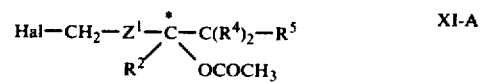
XI-A where the asterisk denotes a carbon atom that is "resolved;" i.e., that is exclusively in either the R or S configuration, and $Z^1$ is ethynylene.

In the synthesis of XI-A, the above-mentioned alcohols

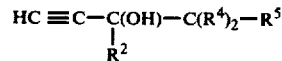

must be resolved into their constituent R and S enantiomers. The methods used for resolution are described fully by A. W. Ingensoll in "Organic Reactions," Vol. II, R. Adams, Ed. John Wiley and Sons, Inc., New York, N.Y., 1944, p. 376. The enantiomeric alcohols, once in hand, are carried forward to intermediates XI-A exactly as described previously.

EXAMPLE 1

Preparation of 4-(4-Acetyl-8-hydroxytridecyl)benzoic Acid

Step A(1): Preparation of p-(3-Bromopropyl)acetophenone

A suspension of aluminum chloride (84 g.; 0.63 mole) in a mixture of acetyl chloride (45 ml.) and carbon disulfide (300 ml.), under nitrogen, is cooled in an ice bath and treated, dropwise, over a 30 minute period, with a mixture of 3-phenylpropyl bromide (119.5 g.; 0.60 mole) and acetyl chloride (93 ml.). At the end of the addition, the temperature is 5°-10° C. and a brown solution is obtained. The cooling bath is removed and stirring is continued at room temperature for 2 hours.

The reaction mixture is poured into a mixture of finely ground ice (600 g.) and concentrated hydrochloric acid (60 ml.). The resulting oil is extracted into ether and the combined extracts are washed well with water and the dried over anhydrous magnesium sulfate. The solvents are removed under reduced pressure, followed by a benzene chaser, to give 105.6 g. (theory 144.68 g.) of light, orange-red residual oil. This oil is distilled from a 250 mg. Claisen, without a column, to give the title compound as a light yellow oil, yield 119.6 g. (83%), b.p. 185°–187° C./14 mm.

Step A(2): Preparation of p-(3-Bromopropyl)benzoic Acid

A solution of sodium hydroxide (163.68 g.; 4.092 moles) in water (1400 ml.) and dioxane (1000 ml.) is chilled in a salt-ice bath to 15° C. and treated, dropwise, over 30 minutes with bromine (238.10 g.; 1.488 moles) at 10°–15° C. Then p-(3-bromopropyl)acetophenone (119.60 g.; 0.496 mole) is added, dropwise, over 1 hour at 5°–10° C., employing good stirring. Stirring at 0°–5° C., is continued until the hypobromite is exhausted. The time required is 2 hours.

The reaction solution is acidified with an excess of concentrated hydrochloric acid. The supernatant is decanted from a semi-solid which separates. The semi-solid is dissolved in ether and the ether solution is washed well with water and then dried over anhydrous magnesium sulfate. The ether is removed under reduced pressure to give a semi-solid residue. The residual semi-solid is stirred with petroleum ether. The resulting white solid is collected by filtration and washed with petroleum ether. The yield of the title compound is 100.8 g. (84%), m.p. 115°–118° C. (Lit. Ref.: F. F. Blicke and under a Dean and Stark constant water separator until the evolution of water ceases. The time required is 23 hours. The cold reaction mixture is washed with water (230 ml.), saturated sodium bicarbonate solution (115 ml.), water (230 ml.) and then dried over anhydrous magnesium sulfate. The solvents are removed under reduced pressure to give 113.4 g. (theory 111.18 g.) of light, orange-red residual oil. This oil is distilled from a 250 ml. Claisen having a 15 cm. Vigreux column to give the title compound as a colorless oil, yield 99.0 g. (89%), b.p. 136°–139° C./0.05 mm.

Step B(1): Preparation of 1-Chloro-4-nonanone

To the Grignard reagent prepared from a mixture of amyl bromide (226.59 g.; 1.5 moles) and magnesium (36.48 g.; 1.5 moles) in ether (1000 ml.) is added, dropwise, during one hour, 4-chlorobutyronitrile (155.34 g.; 1.5 moles). Stirring is continued for an additional one hour. The reaction mixture is poured into a mixture of finely crushed ice (1000 g.) and concentrated hydrochloric acid (750 ml.). The ether layer is separated quickly and discarded. The aqueous layer is heated on a steam bath for one hour to hydrolyze the intermediate imine and cause the separation of the ketone as an oil. After cooling, the oil is extracted with ether and the combined extracts are washed with saturated sodium chloride solution and dried over anhydrous sodium sulfate. The solvent is removed under vacuum and the residual oil is distilled to give 69.0 g. (26%) of colorless oil, b.p. 115°–117° C./14 mm.; pmr (CDCl$_3$) δ0.090 (3H,t), 3.56 (2H,t,CH$_2$Cl).

Step B(2): Preparation of 1-Chloro-4-nonanol

A suspension of sodium borohydride (6.62 g.; 0.175 mole) and sodium hydroxide (1.3 g.) in ethanol (310 ml.) is treated, dropwise, over 1 hour with 1-chloro-4-nonanone (61.40 g.; 0.349 mole) while the temperature is maintained at 45°–50° C. Stirring is continued for one hour, longer without external cooling.

The reaction mixture is acidified with concentrated hydrochloric acid to the Congo red endpoint and then the ethanol is removed under reduced pressure. The residue is treated with water (200 ml.) and the resulting oil is extracted with ether. The combined extracts are washed with saturated sodium chloride solution and dried over anhydrous sodium sulfate. The solvent is removed under vacuum to give the title compound as a light yellow residual oil, yield 58.85 g.; ir (neat) 3400 cm$^{-1}$.

Step B(3): Preparation of 1-Chloro-4-acetoxynonane

A mixture of 1-chloro-4-nonanol (111.99 L g.; 0.627 mole) and acetic anhydride (128.0 g.; 1.254 moles) is heated on a steam bath for 1½ hours.

The volatile materials are removed under reduced pressure and the residual oil is distilled to give 88.6 g. (64%) of colorless oil, b.p. 130°–133° C./14 mm.; pmr (CDCl$_3$) δ0.89 (3H,t), 2.02 (3H, s CH$_3$COO), 3.53 (2H,t CH$_2$Cl), 4.89 (1H,m).

Anan. Calcd. for C$_{11}$H$_{21}$ClO$_2$: C, 59.85; H, 9.59. Found: C, 59.87; H, 9.67.

Step C: Preparation of Ethyl 4-(4-tert.-Butoxycarbonyl-5-oxohexyl)benzoate

A suspension of sodium hydride (57% in mineral oil) (3.967 g. net wt.; 0.165 mole) in a solvent mixture of benzene (75 ml.) (dried over molecular sieves) and dimethylformamide (75 ml.) (dried over molecular sieves), under N$_2$, is treated, dropwise, over 30 minutes with tert.-butyl acetoacetate (23.73 g.; 0.15 mole). Stirring is continued for an additional 30 minutes. Then ethyl p-(3-bromopropyl)benzoate (40.68 g.; 0.15 mole) is added, dropwise, over 15 minutes. A trace of sodium iodide is added and the mixture is heated to 100° C. over 30 minutes and then maintained at 100° C. for 5 hours.

The cooled reaction mixture is treated with water (300 ml.) and the organic layer is treated with water (300 ml.) and the organic layer is separated. The aqueous layer is extracted with ether. The combined organic solutions are washed well with saturated sodium chloride solution and then dried over anhydrous magnesium sulfate. The solvents are removed under reduced pressure, followed by a benzene chaser, to give the title compound as a light, orange-red residual oil, yield 51.13 g. (theory 52.27 g.). This material is used in the next step without purification.

Step D: Preparation of Ethyl 4-(4-Acetyl-4-tert.-butoxycarbonyl-8-acetoxytridecyl)benzoate A suspension of sodium hydride (57% in mineral oil) (3.88 g. net wt.; 0.162 mole) in a solvent mixture of benzene (74 ml.) (dried over molecular sieves) and dimethylformamide (74 ml.) (dried over molecular sieves), under N$_2$, is treated, dropwise, over 30 minutes with ethyl 4-(4-tert.-butoxycarbonyl-5-oxohexyl)benzoate (51.10 g.; 0.147 mole). Stirring is continued for an additional 30 minutes. Then 1-chloro-4-acetoxynonane (35.76 g.; 0.162 mole) is added, dropwise, over 15 minutes. A trace of sodium iodide is added and the mixture is heated to 100° C. over 30 minutes and then maintained at 100° C. for 63½ hours.

The cooled reaction mixture is treated with water (300 ml.) and the organic layer is separated. The aqueous layer is extracted with ether. The combined organic solutions are washed well with saturated sodium chloride solution and then dried over anhydrous magnesium sulfate. The solvents are removed under reduced pressure, followed by a benzene chaser, to give the title compound as a dark, reddish-brown residual oil, yield 78.03 g. (theory 78.31 g.). This material is used in the next step without purification.

Step E: Preparation of Ethyl 4-(4-Acetyl-8-acetoxytridecyl)benzoate

A mixture of ethyl 4-(4-acetyl-4-tert.-butoxycarbonyl-8-acetoxytridecyl)benzoate (78 g.; 0.145 mole), p-toluenesulfonic acid monohydrate (3 g.), acetic acid (300 ml.) and acetic anhydride (15 ml.) is heated on a steam bath for 4 hours. The evolution of gases begins immediately and continues throughout the heating period but becomes very slow after 3 hours.

The cooled reaction mixture is treated with water (500 ml.). The resulting oil is extracted into ether and the combined extracts are washed with water, saturated sodium bicarbonate solution, water, and then dried over anhydrous magnesium sulfate. The solvent is removed under reduced pressure, followed by a benzene chaser, to give 53.7 g. (theory 62.73 g.) of brown residual oil. The oil is purified by column chromatography on silica gel (500 g.) made up in chloroform. The column is eluted with chloroform until the product reaches the bottom of the column and then the elution is continued with 1% methanol in chloroform, collecting 50 ml. fractions. The fractions are examined by TLC using fluorescent silica gel plates and a solvent system of 2% methanol in chloroform. The spots on the developed plates are visible under UV light and also in iodine vapor. Fractions showing a single spot, $R_f$ 0.76, are combined and solvent removed under reduced pressure to give 32.27 g. (51.4%) of the title compound as a light yellow oil. When preparing a sample for analysis, the last traces of solvent are removed in a vacuum at 100° C. by oil pumping for 3 hours.

Anal. Calcd. for $C_{26}H_{40}O_5$: C, 72.19; H, 9.32. Found: C, 72.04; H, 9.30.

Step F: Preparation of 4-(4-Acetyl-8-hydroxytridecyl)benzoic Acid

A solution of ethyl 4-(4-acetyl-8-acetoxytridecyl)benzoate (32 g.; 0.074 mole) in methanol (320 ml.) is treated with a solution of sodium hydroxide (8.8 g.; 0.22 mole) in water (50 ml.) and the resulting solution is heated at 60° C. for 18 hours.

Most of the methanol is removed under reduced pressure. The residual solution is diluted with water (300 ml.) and extracted with ether (to remove any remaining ester). The aqueous layer is acidified with concentrated hydrochloric acid to the Congo Red endpoint. The resulting oil is extracted into ether and the combined extracts are washed well with water and then dried over anhydrous magnesium sulfate. The solvent is removed under reduced pressure, followed by a benzene chaser, to give 20.1 g. (theory 26.82 g.) of yellow residual oil. The oil is purified by column chromatography on silica gel (350 g.) made up in chloroform. The column is eluted with chloroform until the product reaches the bottom of the column and then the elution is continued with 2% methanol in chloroform, collecting 25 ml. fractions. The fractions are examined by TLC using fluorescent silica gel plates and a solvent system of chloroform-methanol-acetic acid (97:2:1). The spots on the developed plates are visible under UV light and also in iodine vapor. Fractions showing a single spot, $R_f$ 0.51, are combined and solvent removed under reduced pressure to give 7.8 g. (29%) of the title compound as a yellow, very viscous oil. When preparing a sample for analysis, the last traces of solvent are removed in a vacuum at 100° C. by oil pumping for 3 hours.

Anal. Calcd. for $C_{22}H_{34}O_4$: C, 72.89; H, 9.45. Found: C, 72.52; H, 9.45.

EXAMPLE 2

Preparation of 4-[(4-(1-Hydroxyethyl)-8-hydroxytridecyl]benzoic Acid 4-(4-Acetyl-8-hydroxytridecyl)benzoic acid (7.2 g., 0.02 mole) is dissolved in a solution of sodium hydroxide (1.2 g., 0.03 mole) in water (80 ml.). Sodium borohydride (0.76 g., 0.02 mole) is added and the resulting solution is let stand at 25°–27° C. for 21 hours. The mixture is then acidified to Congo Red with concentrated hydrochloric acid. The thick oil which separates is taken up in ether, washed with water, and dried over magnesium sulfate. The ether is evaporated and the crude product chromatographed on a column containing 100 g. of silica gel. Elution with 4% methanol in chloroform affords 4.9 g. (68%) of pure 4-[4-(1-hydroxyethyl)-8-hydroxytridecyl]benzoic acid as a colorless viscous oil which gradually partially solidifies to a wax.

Anal. Calcd. for $C_{22}H_{36}O_4$: C, 72.49; H, 9.95. Found: C, 72.11; H, 10.41.

EXAMPLE 3

Preparation of 4-(4-Acetyl-8-hydroxytridec-6-en-1-yl)benzoic Acid

Step A: Preparation of Ethyl 4-(4-Ethoxycarbonyl-5-oxohexyl)benzoate

A suspension of sodium hydride (2.64 g., 0.11 mole) in a solvent mixture of benzene (60 ml.) and dimethylformamide (60 ml.) is treated dropwise over 30 minutes with ethyl acetoacetate (13.0 g., 0.1 mole). Stirring is continued an additional 30 minutes. Then ethyl p-(3-bromopropyl)benzoate (Example 1, Step A(3)) (27.1 g., 0.1 mole) is added dropwise over 15 minutes. The resulting mixture is stirred and heated at 100° C. for 5 hours.

The cooled reaction mixture is treated with water (300 ml.) and the organic layer is separated, diluted with ether, and washed with water and brine. The organic solution is dried over magnesium sulfate. Solvents are removed at reduced pressure to give the title compound as an orange-colored residual oil. This material is used in the next step without purification.

Step B: Preparation of Ethyl 4-(4-Acetyl-4-ethoxycarbonyl-8-acetoxytridec-6-en-1-yl)benzoate A suspension of sodium hydride (2.64 g., 0.11 mole) in a mixture of benzene (60 ml.) and dimethylformamide (60 ml.) is treated dropwise over 30 minutes with ethyl 4-(4-ethoxycarbonyl-5-oxohexyl)benzoate (32.0 g., 0.1 mole). Stirring is continued for an additional 30 minutes. Then, 1-bromo-4- acetoxy-2-nonene (27.1 g., 0.1 mole) is added and the mixture is heated at 100° C. for 8 hours.

The cooled reaction mixture is treated with water (300 ml.), and the organic layer separated, diluted with ether, washed with water and brine, and dried over magnesium sulfate. The solvents are removed at reduced pressure to give the title compound as a red-orange, viscous residual oil. It is used in the next step without purification.

Step C: Preparation of 4-(4-Acetyl-8-hydroxytridec-6-en-1-yl)benzoic Acid

A solution of ethyl 4-(4-acetyl-4-ethoxycarbonyl-8-acetoxytridec-6-en-1-yl)benzoate (50.2 g., 0.1 mole) and sodium hydroxide (28.0 g., 0.7 mole) in water (300 ml.) and ethanol (350 ml.) is boiled under reflux for 3 hours. Solvents are removed under reduced pressure, the residue is dissolved in water, and the solution extracted with ether. The aqueous layer is acidified with concentrated hydrochloric acid to the Congo Red endpoint. The crude product separates as an oil. It is isolated in pure condition by column chromatography on silica gel with 4% methanol in chloroform as the eluant. 4-(4-Acetyl-8-hydroxytridec-6-en-1-yl)benzoic acid is obtained as a yellow, very viscous oil.

EXAMPLE 4

Preparation of 4-(4-Acetyl-8-hydroxy-8-methyltridecyl)benzoic Acid

Step A: Preparation of 1-Chloro-4-acetoxy-4-methylnonane

To the Grignard reagent prepared from 1-bromopentane (4.8 g., 0.04 mole) and magnesium (0.96 g., 0.04 mole) in ether is added 5-chloro-2-pentanone (6.0 g., 0.04 mole). The reaction mixture is stirred at 25° C. for 1 hour and then cooled to 15° C. Acetic anhydride (6 ml., excess) is added carefully and the solution is allowed to stand for 20 hours. Water is added, and the ether layer is separated, washed with brine, and dried over sodium sulfate, Distillation affords the title compound in 4.3 g. (46%) yield, b.p. 88° C. (0.1 mm.).

Anal. Calcd. for $C_{12}H_{23}ClO_2$: C, 61.39; H, 9.87. Found: C, 60.99; H, 10.19.

Step B: Preparation of Ethyl 4-(4-Acetyl-4-ethoxycarbonyl-8-acetoxy-8-methyltridecyl)benzoate This compound is prepared by the method described in Example 3, Step B, except that an equivalent quantity of 1-chloro-4-acetoxy-4-methylnonane is substituted for 1-bromo-4-acetoxy-2-nonene and the heated period is extended to 20 hours. The title compound is obtained as a red, viscous oil which is used in the next step without purification.

Step C: Preparation of 4-(4-Acetyl-8-hydroxy-8-methyltridecyl)benzoic Acid

This compound is prepared by the method described in Example 3, Step C, except that an equivalent quantity of the product of Step B of the present example replaces ethyl 4-(4-acetyl-4-ethoxycarbonyl-8-acetoxytridec-6-en-1-yl)benzoate. The title compound is purified by column chromatography on silica gel with 4% methanol in chloroform as eluant and is obtained as a nearly colorless, viscous oil.

EXAMPLE 5

Preparation of 4-(4-Acetyl-8-hydroxy-9,9-dimethyltridecyl)benzoic Acid

Step A(1): Preparation of 1-Chloro-5,5,-dimethyl-4-nonanone

Four hundred ml. of a solution in ether of 1,1-dimethylpentylmagnesium chloride prepared from magnesium (24.3 g., 1.0 mole) and 1-chloro-1,1-dimethylpentane (134.5 g., 1.0 mole) according to the procedure of Whitmore and Badertscher [J. Am. Chem. Soc., 55, 1559 (1933)] is added dropwise with stirring to 4-chlorobutyryl chloride (197 g., 1.4 moles) in ether (400 ml.) during 6 hours. The reaction mixture is stirred for an additional 12 hours. It is then poured into a mixture of ice and dilute hydrochloric acid. The ether layer is separated, washed with water, and dried over sodium sulfate. The ether is evaporated and the residue distilled at aspirator vacuum through a Vigreaux column to yield the product as a colorless oil.

Step A(2): Preparation of 1-Chloro-5,5-dimethyl-4-nonanol

By following the procedure described for 1-chloro-4-nonanol (Example 1, Step B(2)) but substituting 1-chloro-5,5-dimethyl-4-nonanone for 1-chloro-4-nonanone and continuing stirring and heating at 50° C. for 6 hours, there is obtained 1-chloro-5,5-dimethyl-4-nonanol.

Step A(3): Preparation of 1-Chloro-4-acetoxy-5,5-dimethylnonane

By following the procedure described for 1-chloro-4-acetoxynonane (Example 1, Step B(3)) but substituting 1-chloro-5,5-dimethyl-4-nonanol for 1-chloro-4-nonanol and continuing the steam bath heating for 4 hours, there is obtained 1-chloro-4-acetoxy-5,5-dimethylnonane.

Step B: Preparation of Ethyl 4-(4-Acetyl-4-tert-butoxycarbonyl-8-acetoxy-9,9-dimethyltridecyl)benzoate This compound is prepared by the method described in Example 1, Step D, except that an equivalent quantity of 1-chloro-4-acetoxy-5,5-dimethylnonane is substituted for 1-chloro-4-acetoxynonane. The title compound is obtained as a residual oil which is used in the next step without purification.

Step C: Preparation of Ethyl 4-(4-Acetyl-8-acetoxy-9,9-dimethyltridecyl)benzoate This compound is prepared and purified chromatographically by the method described in Example 1, Step E, except that an equivalent quantity of ethyl 4-(4-acetyl-4-tert-butoxycarbonyl-8-acetoxy-9,9-dimethyltridecyl)benzoate is substituted for the ethyl 4-(acetyl-4-tert-butoxycarbonyl-8-acetoxytridecyl)benzoate of Example 1, Step E.

Step D: Preparation of 4(4-Acetyl-8-hydroxy-9,9-dimethyltridecyl)benzoic Acid This compound is prepared and purified by the method described in Example 1, Step F, except that an equivalent quantity of ethyl 4-(4-acetyl-8-acetoxy-9,9-dimethyltridecyl)benzoate is substituted for the ethyl 4-(4-acetyl-8-acetoxytridecyl)benzoate of Example 1, Step F. The title compound is obtained as a viscous yellowish oil.

EXAMPLE 6

Preparation of 4-(4-Acetyl-8-hydroxypentadecyl)benzoic Acid

This compound is prepared by the method described in Example 1 for 4-(4-acetyl-8-hydroxytridecyl)benzoic acid except that in Step D an equivalent quantity of 1-chloro-4-acetoxyundecane is substituted by 1-chloro- 4-acetoxynonane. The intermediates and final product thus obtained are, Step D: ethyl 4-(4-acetyl-4-tert-butoxycarbonyl-8-acetoxypentadecyl)benzoate; Step E: ethyl 4-(4-acetyl-8-acetoxypentadecyl)benzoate; and Step F: 4-(4-acetyl-8-hydroxypentadecyl)benzoic acid.

EXAMPLE 7

Preparation of 4-(4-Acetyl-8-hydroxy-12-methyltridecyl)benzoic Acid

This compound is prepared by the method described in Example 1 for 4-(4-acetyl-8-hydroxytridecyl)benzoic acid except that in Step D an equivalent quantity of 1-chloro-4-acetoxy-8-methylnonane is substituted for 1-chloro-4-acetoxynonane. The intermediates and final product thus obtained are, Step D: ethyl 4-(4-acetyl-4-tert-butoxycarbonyl-8-acetoxy-12-methyltridecyl)benzoate; Step E: ethyl 4-(4-acetyl-8-acetoxy-12-methyltridecyl)benzoate; and Step F: 4-(4-Acetyl-8-hydroxy-12-methyltridecyl)benzoic acid.

EXAMPLE 8

Preparation of 4-(4-Acetyl-8-hydroxy-12,12-dimethyltridecyl)benzoic Acid

The synthesis of this compound is carried out as described in Example 1, except that in Step B (1) an equivalent amount of 1-bromo-4,4-dimethylpentane is substituted for amyl bromide. The product of Step B (1) thus becomes 1-chloro-8,8-dimethyl-4-nonanone. Subsequent steps afford in order: Step B(2), 1-chloro-8,8-dimethyl-4-nonanol; Step B(3), 1-chloro-4-acetoxy-8,8-dimethylnonane; Step C, ethyl 4-(4-tert-butoxycarbonyl-5-oxohexyl)benzoate (unchanged from Example 1); Step D, ethyl 4-(4-acetyl-4-tert-butoxycarbonyl-8-acetoxy-12,12-dimethyltridecyl)benzoate (by substituting 1-chloro-4-acetoxy-8,8-dimethylnonane for 1-chloro-4-acetoxynonane); Step E, ethyl 4-(4-acetyl-8-acetoxy-12,12-dimethyltridecyl)benzoate; and Step F, 4-(4-acetyl-8-hydroxy-12,12-dimethyltridecyl)benzoic acid, obtained as a viscous yellowish oil.

EXAMPLE 9

Preparation of 4-(4-Acetyl-8-hydroxytridec-12-en-1-yl)benzoic Acid

The synthesis of this compound is carried out as described in Example 1, except that in Step B(1) an equivalent amount of 5-bromo-1-pentene is used in place of amyl bromide. The product of Step B(1) thus becomes 1-chloro-8-nonen-4-one. Subsequent steps afford in order: Step B(2), 1-chloro-8-nonen-4-ol; Step B(3), 1-chloro-4-acetoxy-8-nonene; Step C, ethyl 4-(4-tert-butoxycarbonyl-5-oxohexyl)benzoate (unchanged from Example 1); Step D, ethyl 4-(4-acetyl-4-tert-butoxycarbonyl-8-acetoxytridec-12-en-1-yl)benzoate (by substituting 1-chloro-4-acetoxy-8-nonene for 1-chloro-4-acetoxynonane); Step E, ethyl 4-(4-acetyl-8-acetoxytridec-12-en-1-yl)benzoate; and Step F, 4-(4-acetyl-8-hydroxytridec-12-en-1-yl)benzoic acid, obtained as a viscous yellowish oil.

EXAMPLE 10

Preparation of 4-(4-Acetyl-8-hydroxy-13,13,13-trifluorotridecyl)benzoic Acid

The synthesis of this compound is carried out as described in Example 1, except that in Step B(1) an equivalent amount of 1,1,1-trifluoro-5-bromopentane is substituted for amyl bromide. The product of Step B(1) thus becomes 1-chloro-9,9,9-trifluoro-4-nonanone. Subsequent steps afford in order: Step B(2), 1-chloro-9,9,9-trifluoro-4-nonanol; Step B(3), 1-chloro-4-acetoxy-9,9,9-trifluorononane; Step C, ethyl 4-(4-tert-butoxycarbonyl-5-oxohexyl)benzoate; Step D, ethyl 4-(4-acetyl-4-tert-butoxycarbonyl-8-acetoxy-13,13,13-trifluorotridecyl)benzoate (by substituting 1-chloro-4-acetoxy-9,9,9-trifluorononane for 1-chloro-4-acetoxynonane); Step E, ethyl 4-(4-acetyl-8-acetoxy-13,13,13-trifluorotridecyl)benzoate; and Step F, 4-(4-acetyl-8-hydroxy-13,13,13-trifluorotridecyl)benzoic acid, obtained as a viscous yellow oil.

EXAMPLE 11

Preparation of 4-[4-Acetyl-7-(1-hydroxycylohexyl)-6-heptyn-1-yl]benzoic Acid

Step A: Preparation of Ethyl 4-[4-Acetyl-4-ethoxycarbonyl-7-(1-acetoxycyclohexyl)-6-heptyn-1yl)benzoate Ethyl 4-(4-ethoxycarbonyl-5-oxohexyl)benzoate (Example 3, Step A) (32.0 g., 0.10 mole) is added dropwise to a stirred suspension of sodium hydride (2.6 g., 0.11 mole) in benzene (50 ml.) and dimethylformamide (50 ml.) during 30 minutes. Stirring is continued for an additional 30 minutes. Then, 1-acetoxy-1-(3-bromo-1-propynyl)cyclohexane (28.5 g., 0.11 mole) is added rapidly and the resulting mixture is heated at 95°–97° C. for 3 hours.

The reaction mixture is cooled and treated with 200 ml. of water. The organic layer is separated, diluted with ether, washed with water and brine, and dried over magnesium sulfate. Evaporation of solvents at reduced pressure leaves ethyl 4-[4-acetyl-4-ethoxycarbonyl-7-(1-acetoxycyclohexyl)-6-heptyn-1-yl]benzoate as a red viscous oil which is used in the next step without purification.

Step B: Preparation of 4-[4-Acetyl-7-(1-hydroxycyclohexyl)-6-heptyn-1-yl]benzoic Acid A solution of ethyl 4-[4-acetyl-4-ethoxycarbonyl-7-(1-acetoxycyclohexyl)-6-heptyn-1-yl]benzoate (49.9 g., 0.10 mole) and sodium hydroxide (24 g., 0.6 mole) in water (60 ml.) and methanol (540 ml.) is heated at reflux for 4 hours. Workup of the hydrolysis mixture is carried out as described in Example 3, Step C. The crude acid product which is obtained weighs 35.6 g. It is purified by column chromatography on 535 g. of silica gel with 4% methanol in chloroform as eluant. There is obtained 5.1 g. of the title compound as a yellow viscous oil.

EXAMPLE 12

Preparation of 4-[4-Acetyl-7-(1-hydroxycyclohexyl)heptyl]benzoic Acid

4-[4-Acetyl-7-(1-hydroxycyclohexyl)-6-heptyn-1-yl]benzoic acid (5.1 g., 0.014 mole) in ethyl acetate (55 ml.) is hydrogenated over 2.0 g. of a 5% Pt on charcoal catalyst at 1 atmosphere pressure and room temperature. The theoretical amount of hydrogen (0.028 mole) is absorbed in 25 minutes. The catalyst is filtered off, the solvent is evaporated and the residue (5 g.) is chromatographed on 75 g. of silica gel with 2% methanol in chloroform as eluant. The title compound is obtained as a colorless viscous oil.

EXAMPLE 13

Preparation of 4-(4-Acetyl-8(S)-hydroxytridecyl)benzoic Acid

Step A: Preparation of Ethyl 4-(4-Acetyl-4-ethoxycarbonyl-8(S)-acetoxytridec-6-yn-1-yl)benzoate This compound is prepared by the method described in Example 11, Step A, except that an equivalent amount of 1-bromo-4(S)-acetoxy-2-nonyne is substituted for 1-acetoxy-1-(3-bromo-1-propynyl)cyclohexane. The title compound is obtained as a viscous red oil which is used in the next step without purification.

Step B: Preparation of 4-(4-Acetyl-8(S)-hydroxy-tridec-6-yn-1-yl)benzoic Acid This compound is prepared by the basic hydrolytic method described in Example 11, Step B. The title compound is obtained as a red viscous oil which is purified by column chromatography on silica gel with 4% methanol in chloroform as the eluant. The title compound is thus obtained as a nearly colorless, viscous oil.

Step C: Preparation of 4-(4-Acetyl-8(S)-hydroxytridecyl)benzoic Acid

This compound is prepared by the hydrogenation of the product of Step C using the method described in Example 12. The product is purified by column chromatography on silica gel with 4% methanol in chloroform as the eluant. The title compound is obtained as a colorless, viscous oil.

EXAMPLE 14

Preparation of 4-(4-Acetyl-8(R)-hydroxytridecyl)benzoic Acid

Step A: Preparation of Ethyl 4-(4-Acetyl-4-ethoxycarbonyl-8(R)-acetoxytridec-6-yn-1-yl)benzoate This compound is prepared by the method described in Example 11, Step A, except that an equivalent amountof 1-bromo-4(R)-acetoxy-2-nonyne is substituted for 1-acetoxy-1-(3-bromo-1-propynyl)cyclohexane. The title compound is obtained as a viscous red oil which is used in the next step without purification.

Step B: Preparation of 4-(4-Acetyl-8(R)-hydroxy-tridec-6-yn-1-yl)benzoic Acid This compound is prepared by the basic hydrolytic method described in Example 11, Step B. The title compound is obtained as a red viscous oil which is purified by column chromatography on silica gel with 4% methanol in chloroform as the eluant. The title compound is thus obtained as a nearly colorless, viscous oil.

Step C: Preparation of 4-(4-Acetyl-8(R)-hydroxytridecyl)benzoic Acid

This compound is prepared by the hydrogenation of the product of Step C using the method described in Example 12. The product is purified by column chromatography on silica gel with 4% methanol in chloroform as the eluant. The title compound is obtained as a colorless, viscous oil.

EXAMPLE 15

Preparation of 4-(4-Acetyl-8-hydroxy-9-propoxynonyl)benzoic Acid

Step A-1: Preparation of 1-(2-Tetrahydropyranyloxy)-4-acetoxy-5-propoxy-2-pentyne To the Grignard reagent prepared from magnesium (11.58 g.; 0.476 mole) and bromoethane (51.88 g.; 0.476 mole) in tetrahydrofuran (400 ml.) is added, dropwise, during 30 minutes, a solution of tetrahydro-2-(2-propynyloxy)-2H-pyran (64.06 g.; 0.457 mole) in tetrahydrofuran (40 ml.). The mixture is stirred at room temperature, under nitrogen, for 1 hour, then chilled in an ice bath and treated, dropwise, during 30 minutes, with a solution of propoxyacetaldehyde (40.5 g.; 0.397 mole) in tetrahydrofuran (60 ml.). The mixture is heated on a steam bath, under nitrogen, for 1 hour, then again chilled in an ice bath and treated, dropwise, during 30 minutes, with a mixture of acetic anhydride (48.60 g.; 0.476 mole) and pyridine (75.31 g.; 0.952 mole). The mixture is heated on a steam bath, under nitrogen for 30 minutes.

The mixture is poured into cold water (1200 ml.) and the organic layer is separated. The aqueous layer is extracted with ether. The combined organic extracts are washed with water and then dried over anhydrous magnesium sulfate. The solvent is removed under vacuum to give the title compound as an orange-red residual oil.

Step A-2: Preparation of 1-(2-Tetrahydropyranyloxy)-4-acetoxy-5-propoxypentane 1-(2-Tetrahydropyranyloxy)-4-acetoxy-5-propoxy-2-pentyne (10.8 g., 0.04 mole) is dissolved in ethyl acetate (100 ml.). 5% Palladium on carbon is added and the mixture is hydrogenated on the Parr apparatus at an initial pressure of 41 lbs./in$^2$ and 25° C. When 0.08 mole of hydrogen is absorbed, the catalyst is removed by filtration and the solvent is evaporated under vacuum to give the title compound as a light orange residual oil.

Step A-3: Preparation of 4-Acetoxy-5-propoxy-1-pentanol

A mixture of 1-(2-tetrahydropyranyloxy-4-acetoxy-5-propoxypentane (11.5 g., 0.42 mole), methanol (700 ml.), concentrated hydrochloric acid (3 ml.) and ethyl acetate (70 ml.) is stirred at room temperature for 1 hour. The reaction mixture is poured into cold H$_2$O (1500 ml.) and the organic layer is extracted with ether. The combined extracts are washed with saturated sodium bicarbonate solution, then brine, and dried over anhydrous magnesium sulfate. The solvent is removed under vacuum and the residual oil is distilled to give the title compound as a light yellow oil.

Step A-4: Preparation of 4-Acetoxy-5-propoxy-1-pentanol Tosylate

A solution of p-toluenesulfonyl chloride (42.0 g., 0.22 mole) in pyridine (100 ml.) is cooled in an ice bath while 4-acetoxy-5-propoxy-1-pentanol (36.8 g., 0.193 mole) is added dropwise with stirring during 40 minutes. The ice bath is replaced by a cool (20° C.) water bath and stirring is continued for 2 hours. The mixture is then poured into 500 ml. of water. The oily product is taken up in ether, washed with 2N hydrochloric acid and water, and dried over sodium sulfate. The solvent is distilled in vacuo to leave the crude title compound as a yellow oil.

Step A-5: Preparation of 4-Acetoxy-5-propoxy-1-iodopentane

A solution of 4-acetoxy-5-propoxy-1-pentanol tosylate (61.5 g., 0.179 mole) and sodium iodide (79.5 g., 0.53 mole) in acetone (500 ml.) is allowed to stand at 25°–27° C. for 18 hours. The precipitated sodium tosylate is filtered off. Most of the acetone is evaporated from the filtrate and the residue is treated with 300 ml. of water. The oily product is taken up in ether, washed with dilute sodium thiosulfate solution, water, and brine, and dried over sodium sulfate. The solvent is distilled in vacuo to give a quantitative yield of the crude title compound as a yellowish oil which is used without further purification.

Step B: Preparation of Ethyl 4-(4-Acetyl-4-t-butoxycarbonyl-8-acetoxy-9-propoxynonyl)benzoate This compound is prepared by the method described in Example 1, Step D, except that an equivalent amount of 4-acetoxy-5-propoxy-1-iodopentane is substituted for 1-chloro-4-acetoxynonane and sodium iodide is omitted. The title compound is obtained as a dark red residual oil which is used in the next step without purification.

Step C: Preparation of Ethyl 4-(4-Acetyl-8-acetoxy-9-propoxynonyl)benzoate

This compound is prepared by the method described in Example 1, Step E, except that the product of Step B of the present example replaces ethyl 4-(4-acetyl-8-acetoxytridecyl)benzoate. The title compound is purified by column chromatography on silica gel and is obtained as a yellowish, viscous oil.

Step D: Preparation of 4-(4-Acetyl-8-hydroxy-9-propoxynonyl)benzoic Acid

This compound is prepared by the method described in Example 1, Step F, except that the product of Step C of the present example replaces ethyl 4-(4-acetyl-8-acetoxytridecyl)benzoate. The title compound is purified by column chromatography on silica gel with 4% methanol in chloroform as the eluant. The title compound is a light yellow, viscous oil.

EXAMPLE 16

Preparation of 4-(4-Propionyl-8-hydroxytridecyl)benzoic Acid

Step A: Preparation of Ethyl 4-(4-Ethoxycarbonyl-5-oxoheptyl)benzoate

This compound is prepared by the method described in Example 3, Step A, except that an equivalent quantity of ethyl propionylacetate is substituted for ethyl acetoacetate. The title compound is obtained as a reddish residual oil which is used in the next step without purification.

Step B: Preparation of Ethyl 4-(4-Ethoxycarbonyl-4-propionyl-8-acetoxytridecyl)benzoate This compound is prepared by the method of Example 3, Step B, except that the product of Step A of the present example replaces ethyl 4-(4-ethoxycarbonyl-5-oxohexyl)benzoate of Example 3. The title compound, obtained as a red residual oil, is used in the next step without purification.

Step C: Preparation of 4-(4-Propionyl-8-hydroxytridecyl)benzoic Acid

This product is prepared by the hydrolytic method described in Example 3, Step C, from the crude product of Step B of the present example. The title product is purified by column chromatography on silica gel with 4% methanol in chloroform as eluant. It is a nearly colorless, viscous oil.

EXAMPLE 17

Preparation of Methyl 4-(4-Acetyl-8-hydroxytridecyl)benzoate

A solution of diazomethane (approximately 2.5 g., 0.06 mole) in ether (100 ml.) is mixed with a solution of 4-(4-acetyl-8-hydroxytridecyl)benzoic acid (10.8 g., 0.03 mole) in ether (50 ml.). The resulting solution is allowed to stand 4 hours at room temperature. Acetic acid is then added to destroy the excess diazomethane and the solution is washed with dilute sodium bicarbonate solution and water and dried over sodium sulfate. Evaporation of volatile materials at reduced pressure yields methyl 4-(4-acetyl-8-hydroxytridecyl)benzoate, a colorless viscous oil.

EXAMPLE 18

Preparation of N-(2-Dimethylaminoethyl)-4-(4-acetyl-8-hydroxytridecyl)benzamide A solution of 4-(4-acetyl-8-hydroxytridecyl)benzoic acid (3.62 g., 10 millimole), Example 1, Step F, triethylamine (1.74 ml., 12.5 millimole), and distilled water (18 ml., 1.0 mole) in acetonitrile (100 ml.) is treated with N-t-butyl-5-methylisoxazolium perchlorate (3.0 g., 12.5 millimole). The resulting solution is evaporated in vacuo (water aspirator) at 20°–23° C. for 4 hours providing a tacky residue which is triturated with water (150 ml.) at 0°–5° C. for 15 minutes. After decanting the aqueous phase, the oily residue is dissolved in benzene-ether (1:1) (200 ml.). The organic extract is dried over sodium sulfate, filtered, and evaporated in vacuo at 35°–40° C. providing the desired active ester, N-t-butyl-3-[4-(4-acetyl-8-hydroxytridecyl)benzoyloxy]crotonamide, as a pale yellow oil.

A solution of 2-dimethylaminoethylamine (0.88 g., 10 millimole) in acetonitrile (25 ml.) is added to a solution of the "active ester" in acetonitrile (25 ml.) providing a clear solution which is stirred at 25° C. for 17 hours. The solvent is removed in vacuo at 40°–50° C. leaving a residual oil which is partitioned between ether (200 ml.) and water (2 × 100 ml.). The organic extract is washed with saturated brine (2 × 100 ml.), dried over sodium sulfate, filtered, and evaporated in vacuo at 40°–50° C., providing a tan crude oil.

The oil is partitioned between 5% hydrochloric acid (100 ml.) and ether (2 × 100 ml.). The aqueous acid phase is slowly basified with sodium bicarbonate (16.8 g., 0.2 mole), then with 40% aqueous sodium hydroxide (10 ml.) providing a heterogeneous mixture which is extracted with ether (200, 100 ml.). The organic extract is washed with saturated brine (200 ml.), dried over sodium sulfate, filtered, and evaporated in vacuo at 40°–50° C. leaving the title compound as a pale yellow oil.

EXAMPLE 19

Preparation of 4-(4-Acetyl-8-hydroxytridecyl)benzoic Acid Hydrazide

This compound is prepared essentially by the same procedure as described in Example 18 except hydrazine is used rather than the aliphatic amine and the acid-hydrazine conjugation is effected at −15° C. employing the following reagents:

| | |
|---|---|
| 4-(4-Acetyl-8-hydroxytridecyl)-benzoic Acid (Example 1, Step F) | 3.62 g., 0.01 mole |
| Triethylamine | 1.74 ml., 0.0125 mole |
| Distilled water | 18 ml., 1.0 mole |
| N-t-Butyl-5-methyl-isoxazolium perchlorate | 3.0 g., 0.0125 mole |
| Acetonitrile | 150 ml. |
| Hydrazine . hydrate | 0.5 g., 0.01 mole |

The title compound is obtained as a pale yellow oil.

EXAMPLE 20

Preparation of 4-(4-Acetyl-8-acetoxytridecyl)benzoic Acid

A mixture of 4-(4-acetyl-8-hydroxytridecyl)benzoic acid (9.0 g., 0.025 mole) and acetic anhydride (6.1 g., 0.06 mole) is heated at 60° C. for 18 hours. The mixture is then cooled and dissolved in 80 ml. ethyl ether. The solution is extracted with an ice-cold solution of 8 g. sodium hydroxide in 150 ml. water. The basic solution is separated and acidified with concentrated hydrochloric acid. The oily acid which separates is taken up in ether, washed with water, and dried over sodium sulfate. The ether is evaporated to leave the oily crude product.

The product is purified by chromatography on a column containing 150 g. of silica gel and with 3% methanol in chloroform as the eluting solvent. There is obtained the title compound as a colorless, viscous oil.

EXAMPLE 21

Preparation of 3-(4-Acetyl-8-hydroxy-1-tridecenyl)benzoic Acid

Step A(1): Preparation of Ethyl 3-(1-Propenyl)benzoate (3-Methoxycarbonylbenzyl)triphenylphosphonium bromide (54.1 g. 0.11 mole) is suspended with stirring in a mixture of acetaldehyde (5.8 g., 0.132 mole) and ethanol (250 ml.). A solution of sodium (2.5 g., 0.11 mole) in ethanol (300 ml.) is added dropwise during 30 minutes. The reaction mixture is stirred an additional 4 hours at room temperature and then concentrated to about ¼ volume at reduced pressure. Water (150 ml.) is added to the residue and the oily product taken up in ether an dried over magnesium sulfate. Ether is evaporated. The residue is treated with 100 ml. of petroleum ether. Insoluble triphenylphosphine oxide is filtered off and the filtrate distilled in vacuo to yield 14.0 g. (72%) of ethyl 3-(1-propenyl)benzoate, b.p. 85°-87° C.. (0.1 mm.). Note that the product is an ethyl ester as a result of transesterification with solvent ethanol during the reaction.

Step A(2): Preparation of Ethyl 3-(3-Bromo-1-propenyl)benzoate

A mixture of ethyl 3-(1-propenyl)benzoate (14.0 g., 0.074 mole), N-bromosuccinimide (14.9 g., 0.084 mole), benzoyl peroxide (150 mg.), and carbon tetrachloride (75 ml.) is stirred and heated at reflux for 46 hours. The mixture is cooled. Solids are filtered off and the filtrate is washed with water and dried over magnesium sulfate. The solvent is evaporated and the residual oil distilled to yield 10.2 g. (51%) of ethyl (3-(3-bromo-1-propenyl)-benzoate, b.p. 129°-131° C. (0.05 mm.).

Step B: Preparation of 3-(4-Acetyl-8-hydroxy-1-tridecen-yl)benzoic Acid

This compound is prepared by the series of reactions described in Example 1, Steps C to F, except that in Step C an equivalent quantity of ethyl 3-(3-bromo-1-propenyl)benzoate is substituted for ethyl p-(3-bromopropyl)benzoate. Thus there are obtained is succession: ethyl 3-(4-butoxycarbonyl-5-oxo-1-hexenyl)benzoate (Step C); ethyl 3-(4-acetyl-4-t-butoxycarbonyl-8-acetoxy-1-tridecenyl)benzoate (Step D); ethyl 3-(4-acetyl-8-acetoxy-1-tridecenyl)benzoate (Step E); and 3-(4-acetyl-8-hydroxy-1-tridecenyl)benzoic acid (Step F).

EXAMPLE 22

Preparation of 3-(4-Acetyl-8-hydroxytridecyl)benzoic Acid 3-(4-Acetyl-8-hydroxy-1-tridecenyl)benzoic acid (7.2 g., 0.02 mole) in ethanol (75 ml.) is hydrogenated over 1.5 g. of a 5% Pd on charcoal catalyst at 1 atmosphere pressure and room temperature. When the theoretical amount (0.02 mole) of hydrogen has been absorbed, the catalyst is filtered off, the solvent evaporated, and the residue chromatographed on silica gel with 4% methanol in chloroform as the eluant. The title compound is obtained as a colorless, viscous oil.

EXAMPLE 23

Preparation of 3-[4-(2-Acetyl-6-hydroxyundecyl)phenyl]propionic Acid

Step A: Preparation of Ethyl p-(Bromomethyl)cinnamate

A mixture of ethyl p-methylcinnamate (19.0 g., 0.1 mole), N-bromosuccinimide (19.6 g., 0.11 mole), benzoyl peroxide (200 mg.), and carbon tetrachloride is stirred and heated at reflux for 4 hours. The mixture is cooled and succinimide removed by filtration. The filtrate is washed with 5% sodium hydroxide solution, water, and brine, and dried over sodium sulfate. The solvent is removed at reduced pressure, and the residue is distilled in vacuo to yield 14.8 g. (55%) of the title compound, b.p. 137°-140° C. (0.1 mm.).

Step B: Preparation of p-(2-Acetyl-6-hydroxyundecyl)cinnamic Acid

This compound is prepared by the series of reactions described in Example 1, Steps C through F, except that in Step C an equivalent quantity of ethyl p-(bromomethyl)cinnamate is substituted for ethyl p-(3-bromopropyl)benzoate. The new compounds thus obtained are: ethyl p-(2-t-butoxycarbonyl-3-oxobutyl)cinnamate (Step C); ethyl p-(2-acetyl-2-t-butoxycarbonyl-6-acetoxyundecyl)cinnamate (Step D); ethyl p-(2-acetyl-6-acetoxyundecyl)cinnamate (Step E); and p-(2-Acetyl-6-hydroxyundecyl)cinnamic acid (Step E). The last-named goal compound is purified by column chromatography on silica gel with 2% methanol in chloroform as the eluant. It is obtained as a waxy solid, m.p. 87°-92° C.

Anal. Calcd. for $C_{22}H_{32}O_4$: C, 73.30; H, 8.95. Found: C, 73.49; H, 8.97.

Step C: Preparation of 3-[4-(2-Acetyl-6-hydroxyundecyl)phenyl]propionic Acid p-(2-Acetyl-6-hydroxyundecyl)cinnamic acid (2.6 g., 0.0072 mole) in ethanol (30 ml.) is hydrogenated over 0.7 g. of a 5% Pd on charcoal catalyst at 1 atmosphere pressure and room temperature. The theoretical amount of hydrogen (0.0072 mole) is absorbed in 7 minutes. The catalyst is filtered off, solvent removed in vacuo, and the residue chromatographed on 45 g. of silica gel with 2% methanol in chloroform elution. The title compound is obtained as a colorless, viscous oil.

Anal. Calcd. for $C_{22}H_{34}O_4$: C, 72.89; H, 9.45. Found: C, 72.51; H, 9.46.

EXAMPLE 24

Preparation of [4-(2-Acetyl-6-hydroxyundecyl)phenoxy]acetic Acid

This compound is prepared by the series of reactions described in Example 1, Steps B through F, except that in Step C an equivalent quantity of the known ethyl 4-chloromethylphenoxyacetate is substituted for ethyl p-(3-bromopropyl)benzoate. The product of Step C is thus ethyl [4-(2-t-butoxycarbonyl-3-oxobutyl)phenoxy]acetate. The products obtained in subsequent steps are: Step D, ethyl [4-(2-acetyl-2-t-butoxycarbonyl-6-acetoxyundecyl)phenoxy]acetate; Step E, ethyl [4-(2-acetyl-6-acetoxyundecyl)phenoxy]acetate; and Step F, [4-(2-acetyl-6-hydroxyundecyl)phenoxy]acetic acid.

EXAMPLE 25

Preparation of [4-(3-Acetyl-7-hydroxydodecyl)phenyl]acetic Acid

Step A(1): Preparation of [4-(2-Bromoethyl)phenyl]acetonitrile

A mixture of p-cyanomethylhydrocinnamic acid (18.9 g., 0.1 mole), red mercuric oxide (17.2 g., 0.08 mole), and carbon tetrachloride (180 ml.) is stirred at room temperature while bromine (16.0 g., 0.1 mole) is added dropwise during 40 minutes. The resulting mixture is heated at reflux for 1 hour. The mixture is then cooled, filtered, washed with dilute hydrochloric acid and water, and dried over magnesium sulfate. The solution is evaporated to leave the product as a yellow residual oil. It is purified by column chromatography on silica gel with benzene elution.

Step A(2): Preparation of [4-(2-Bromoethyl)phenyl]acetic Acid

A solution of [4-(2-bromoethyl)phenyl]acetonitrile (56.0 g., 0.25 mole) in 48% hydrobromic acid (200 ml.) and acetic acid (600 ml.) is boiled under reflux for 4 hours. The solution is reduced to one-third volume by distillation at reduced pressure. The residue is diluted with 400 ml. of water to force out the oily product which is taken up in ether, washed with water, and dried over sodium sulfate. Evaporation of the solvent leaves the title compound as a residual oil.

Step A(3): Preparation of Ethyl [4-(2-Bromoethyl)phenyl]acetate

A solution of [4-(2-bromoethyl)phenyl]acetic acid (48.6 g., 0.2 mole) and sulfuric acid (1.5 ml.) in ethanol (400 ml.) is boiled under reflux for 6 hours. About 300 ml. of the ethanol is removed by distillation at reduced pressure. The residue is diluted with 400 ml. of water. The oily ester is taken up in ether, washed with water and brine, and dried over magnesium sulfate. Evaporation of the ether leaves the title compound as an oil which can be purified by distillation in vacuo.

Step B: Preparation of [4-(3-Acetyl-7-hydroxydodecyl)phenyl]acetic Acid

This compound is prepared by the series of reactions described in Example 1, Steps C to F, except that in Step C an equivalent amount of ethyl [4-(2-bromoethyl)phenyl]acetate is substituted for ethyl p-(3-bromopropyl)benzoate. Thus, there are obtained in succession: ethyl [4-(3-t-butoxycarbonyl-4-oxopentyl)phenyl]acetate (Step C); ethyl [4-3-t-butoxycarbonyl-3-acetyl-7-acetoxydodecyl)phenyl]acetate (Step D); ethyl [4-(3-acetyl-7-acetoxydodecyl)phenyl]acetate (Step E); and [4-(3-acetyl-7-hydroxydodecyl)phenyl]acetic acid (Step F). The title compound is purified by column chromatography on silica gel with 4% methanol in chloroform elution and is obtained as a yellowish, viscous oil.

EXAMPLE 26

Preparation of [2-(4-Acetyl-8-hydroxytridecyl)phenyl]acetic Acid

Step A(1): Preparation of Ethyl o-(cyanomethyl)cinnamate

A solution of ethyl o-(bromomethyl)cinnamate (94.1 g., 0.35 mole), and sodium cyanide (20.6 g., 0.42 mole) in ethanol (450 ml.) is heated at reflux for 3 hours. About half of the ethanol is removed at reduced pressure. To the residue is added 500 ml. of water. The oily product is taken up in ether, washed with water, and dried over magnesium sulfate. Evaporation of the ether affords the title compound as an oil.

Step A(2): Preparation of Ethyl o-(Cyanomethyl)hydrocinnamate

Ethyl o-(cyanomethyl)cinnamate (75.1 g., 0.35 mole) is dissolved in ethanol (300 ml.) and hydrogenated at a pressure of b 1 atmosphere and room temperature over 2.5 g. of a 5% palladium on charcoal catalyst. When the theoretical amount of hydrogen (0.35 mole) has been absorbed, the catalyst is filtered off and the ethanol removed by distillation at reduced pressure to yield ethyl o-(cyanomethyl)hydrocinnamate.

Step A(3): Preparation of [2-(3-Hydroxypropyl)phenyl]acetonitrile

A 70% solution in benzene of sodium bis(2-methoxyethoxy)aluminum hydride (95.2 g., 0.33 mole of reagent) is added dropwise during one hour to a stirred solution of ethyl o-(cyanomethyl)hydrocinnamate (65.0 g., 0.3 mole) in benzene (250 ml.). The reaction mixture is held at 25°-28° C. by means of a cold water bath. The mixture is stirred at 25°-28° C. for 4 additional hours. Ethyl acetate (5 ml.) is added to destroy excess reducing agent. The mixture is then treated with 250 ml. ice-cold 5% hydrochloric acid. The benzene layer is separated, washed with water, and dried over sodium sulfate. Evaporation of the benzene in vacuo affords [2-(3-hydroxypropyl)phenyl]acetonitrile.

Step A(4): Preparation of [2-(3-Hydroxypropyl)phenyl]acetic Acid

A solution of [2-(3-hydroxypropyl)phenyl]acetonitrile (52.5 g., 0.30 mole) and sodium hydroxide (40 g., 1.0 mole) in water (200 ml.) and ethanol (600 ml.) is heated at reflux for 18 hours. The solution is concentrated in vacuo to about half-volume. Water (600 ml.) is added and the resulting solution is acidified with 6N hydrochloric acid. The precipitated product acid is taken up in ether, washed with water, and dried over magnesium sulfate. The ether is evaporated in vacuo to afford [2-(3-hydroxypropyl)phenyl]acetic acid.

Step A(5): Preparation of Ethyl [2-(3-Hydroxypropyl)phenyl]acetate

A solution of [2-(3-hydroxypropyl)phenyl]acetic acid (48.6 g., 0.25 mole) and sulfuric acid (3 ml.) in ethanol (400 ml.) is heated at reflux for 6 hours. Workup as described in Example 25, Step A(3) yields the title compound.

Step A(6): Preparation of Ethyl [2-(3-Bromopropyl)phenyl]acetate

To a solution of ethyl [2-(3-hydroxypropyl)phenyl]acetate (44.4 g., 0.20 mole) in ether (300 ml.) is added dropwise during 40 minutes a solution of phosphorus tribromide (20.7 g., 0.075 mole) in ether (100 ml.). The temperature is maintained at 25°-28° C. during this time by means of a cold water bath. The reaction solution is then heated at reflux for 4 hours. It is cooled and poured into iced-water. The ether layer is separated, washed with water, dried over magnesium sulfate, and evaporated in vacuo to yield ethyl [2-(3-Bromopropyl)phenyl]acetate.

Step B: Preparation of [2-(4-Acetyl-8-hydroxytridecyl)phenyl]acetic Acid

This compound is prepared by the series of reactions described in Example 1, Steps C to F, except that in Step C an equivalent quantity of ethyl [2-(3-bromopropyl)phenyl]acetate is substituted for ethyl p-(3-bromopropyl)benzoate. Thus, there are obtained in succession: ethyl [2-(4-t-butoxycarbonyl-5-oxohexyl)phenyl]acetate (Step C); ethyl [2-(4-t-butoxycarbonyl-8-acetoxytridecyl)phenyl]acetate (Step D); ethyl [2-(4-acetyl-8-acetoxytridecyl)phenyl]acetate (Step E); and [2-(4-acetyl-8-hydroxytridecyl)phenyl]acetic acid (Step F).

What is claimed is:

1. The compound having the following formula:

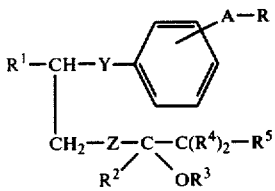

wherein

R is carboxy, a carboxy salt, or derivatized carboxy of the formula COOE wherein E is alkyl of 1 to 10 carbon atoms;

A is $(CH_2)_n$ where n is 0, 1, or 2, and oxymethylene $(—O—CH_2)$;

Y is $(CH_2)_n$ where n is 1, 2, or 3, and $—CH_2—CH=CH—$; and A and Y are in the ortho, meta, or para orientation;

$R^1$ is acetyl, propionyl, butyryl, 1-hydroxyethyl, 1-hydroxypropyl, or 1-hydroxybutyl;

Z is ethylene, vinylene, or ethynylene;

$R^2$ is independently hydrogen or methyl;

$R^3$ is hydrogen;

$R^4$ is selected independently from the group consisting of hydrogen or methyl; and $R^5$ taken together with $R^2$ is a carbocyclic ring with from 5 to 9 members.

2. The compound of claim 1 wherein R is carboxy or a pharmaceutically acceptable carboxy salt.

3. The compound of claim 2 which has the formula:

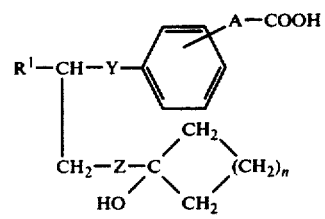

wherein

A is $(CH_2)_n$ where n is 0, 1, or 2 or oxymethylene;

Y is $(CH_2)_n$ where n is 1, 2, or 3 and $—CH_2—CH=CH$; and A and Y are in the ortho, meta, or para orientation;

$R^1$ is acetyl, propionyl, butyryl, 1-hydroxyethyl, 1-hydroxypropyl, or 1-hydroxybutyl;

Z is ethylene, vinylene, or ethynylene; and n is an integer of from 2 to 6.

4. 4-[4-Acetyl-7-(1-hydroxycyclohexyl)heptyl]-benzoic acid, the compound of claim 3 wherein A is $(CH_2)_o$, Y is $(CH_2)_3$, and A and Y are in the para orientation, $R^1$ is acetyl, Z is ethylene, and N is 3.

5. 4-[4-Acetyl-7-(1-hydroxycyclohexyl)-6-heptyn-1-yl]benzoic acid, the compound of claim 3 wherein A is $(CH_2)_o$, Y is $(CH_2)_3$, and A and Y are in the para orientation, $R^1$ is acetyl, Z is ethynylene, and n is 3.

6. The compound of claim 2 which has the formula:

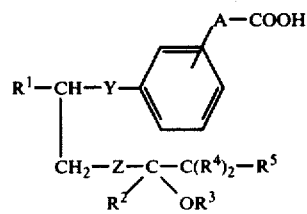

wherein

A is $(CH_2)_n$ where n is 0, 1 or 2 or oxymethylene;

Y is $(CH_2)_n$ where n is 1, 2, or 3, and $—CH_2—CH=CH—$; and A and Y are in the ortho, meta, or para orientation;

$R^1$ is acetyl, propionyl, or butyryl;

Z is ethylene, vinylene, or ethynylene;

$R^2$ is hydrogen or methyl;

$R^3$ is lower alkanoyl;

$R^4$ is hydrogen or methyl; and $R^5$ taken together with $R^2$ is a carbocyclic ring with from 5 to 9 members.

7. The compound of claim 2 which has the formula:

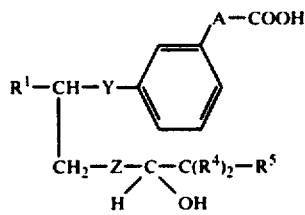

wherein
A is $(CH_2)_n$ where n is 0, 1 or 2 or oxymethylene;
Y is $(CH_2)_n$ where n is 1, 2 or 3 or $-CH_2-CH=CH-$;
$R^1$ is acetyl, propionyl, butyryl, 1-hydroxyethyl, 1-hydroxypropyl, or 1-hydroxybutyl;
Z is ethylene, vinylene, or ethynylene;
$R^4$ is hydrogen or methyl; and
$R^5$ taken together with $R^2$ is a carbocyclic ring with from 5 to 9 members.

8. The compound of claim 2 which has the formula:

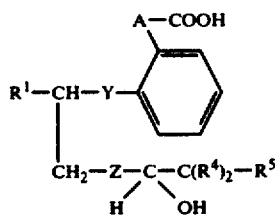

wherein
A is $(CH_2)_n$ where n is 0, 1, or 2 or oxymethylene;
Y is $(CH_2)_n$ where n is 1, 2, or 3 or $-CH_2-CH=CH-$;
$R^1$ is acetyl, propionyl, butyryl, 1-hydroxyethyl, 1-hydroxypropyl, or 1-hydroxybutyl;
Z is ethylene, vinylene, or ethynylene;
$R^4$ is hydrogen or methyl; and
$R^5$ taken together with $R^2$ is a carbocyclic ring with from 5 to 9 members.

9. The compound of claim 1 which has the formula:

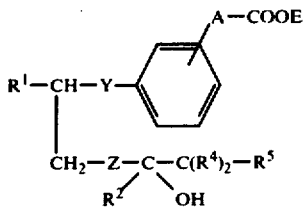

wherein
A is $(CH_2)_n$ where n is 0, 1 or 2;
Y is $(CH_2)_n$ where n is 1, 2, or 3;
and A and Y are in the ortho, meta, or para orientation;
$R^1$ is acetyl, propionyl, or butyryl;
Z is ethylene, vinylene, or ethynylene;
$R^2$ is methyl or hydrogen;
$R^4$ is selected independently from the group consisting of hydrogen and methyl;
$R^5$ taken together with $R^2$ is a carbocyclic ring with from 5 to 9 members; and
E is alkyl having from 1 to 10 carbon atoms.

10. A composition comprising the compound of claim 1 in a non-toxic, pharmaceutically acceptable carrier.

11. The composition of claim 10 which is suitable for oral administration in tablet form.

12. The composition of claim 10 which is suitable for oral adminstration in capsule form.

13. The composition of claim 10 which is suitable for parenteral administration.

14. The composition of claim 10 which is suitable for use in suppository form.

* * * * *